United States Patent [19]
Karami

[11] 3,950,824
[45] Apr. 20, 1976

[54] PRESSURE SENSITIVE DIAPER FASTENER

[75] Inventor: Hamzeh Karami, Crystal Lake, Ill.

[73] Assignee: The Kendall Company, Walpole, Mass.

[22] Filed: Nov. 12, 1974

[21] Appl. No.: 523,033

[52] U.S. Cl. .......................... 24/67 AR; 24/DIG. 11
[51] Int. Cl.² .................... A61F 13/00; B42F 1/00
[58] Field of Search ..... 24/67 AH, DIG. 11, 67 AR, 24/7

[56] References Cited
UNITED STATES PATENTS

| | | | |
|---|---|---|---|
| 273,902 | 3/1883 | Shirley | 24/DIG. 11 |
| 2,521,296 | 9/1950 | Kinney | 24/67 AR |
| 2,902,734 | 9/1959 | Walters | 24/7 |
| 3,031,359 | 4/1962 | Blank et al. | 24/DIG. 11 |
| 3,065,101 | 11/1962 | Phipps | 24/67 R |
| 3,138,476 | 6/1964 | Phipps | 24/67 AH |
| 3,257,677 | 6/1966 | Batchelder et al. | 24/DIG. 11 |
| 3,398,438 | 8/1968 | Fried et al. | 24/7 |

Primary Examiner—Donald A. Griffin

[57] ABSTRACT

A diaper fastener comprising a length of web having a surface which includes a plurality of longitudinally aligned zones. A first end zone is secured to a first portion of the diaper and a second end zone is coated with an adhesive whereby it is securable to a second portion of the diaper for retaining the diaper on an infant. Third, fourth, and fifth intermediate zones are provided with the fifth zone being coated with an adhesive. Each of the third and fourth zones have a limited affinity for the adhesive employed in the second and fifth zones and the web is folded such that the second and third zones are in contact and the fourth and fifth zones are in contact.

12 Claims, 6 Drawing Figures

PRESSURE SENSITIVE DIAPER FASTENER

BACKGROUND OF THE INVENTION

This invention relates to diaper fasteners and, in particular, to fasteners of the type which employ an adhesive-coated web or tape.

It is a principle object of the present invention to provide an improved diaper fastener of this general type in which the tape is stored for use in a neat and convenient configuration and in which an adhesive coated tape portion is easily exposed from the fastener's pre-use configuration for securing the diaper to an infant.

SUMMARY OF THE INVENTION

To achieve these and other objects as shall further appear, a diaper fastener according to the present invention comprises a length of web having a surface comprising a plurality of longitudinally aligned zones including a first end zone secured to a first portion of the diaper and a second end zone coated with an adhesive and securable to a second portion of the diaper. Third, fourth, and fifth intermediate zones are provided, the fifth zone being coated with an adhesive. Each of the third and fourth zones has a limited affinity for the adhesive employed in the fastener. The web is folded such that the second and third zones are in contact and the fourth and fifth zones are in contact. Preferably the third zone has a lesser affinity than does the fourth zone, whereby the limited affinity for adhesive of the fourth zone releasably retains the fastener in the folded condition prior to use while the lesser affinity of the third zone for the adhesive permits the easy grasping of the web in the second zone permitting manual unfolding of the web for actual use of the fastener. While the third and fourth zones may simply be adhesive-free, specially treated areas of the principle web itself, they may also be formed by the application of second and third webs (e.g., papers) to the appropriate zones of a fully adhesive-coated primary web surface. The web applied to form the third zone would have an untreated surface for contact with the adhesive and an upper surface treated to have a very limited affinity for the adhesive. The web applied to form the fourth zone would also have an untreated lower surface for contact with the adhesive on the primary web and would have an upper surface treated to have a reduced affinity for the adhesive, but a greater affinity than the upper surface of the web in the third zone.

In preferred embodiments of the invention the second and third zones have substantially the same longitudinal dimensions along the web and the fourth and fifth zones have substantially the same longitudinal dimensions along the web, whereby those paired zones are completely aligned when the web is folded about a fold line at the margin between the fourth and fifth zones. It is also preferred that the third zone be substantially greater in longitudinal dimension than the fourth zone, thereby providing a larger adhesive-free region for facilitating the aforementioned unfolding of the web and also reducing the likelihood of contact of adhesive with the infant's skin after application of the diaper to an infant.

BRIEF DESCRIPTION OF THE DRAWING

Other objects, features, and advantages of the invention will appear from the following description of particular preferred embodiments of the invention taken together with the accompanying drawings, in which the dimensions of various materials have been exaggerated for clarity. In the drawings.

DETAILED DESCRIPTION OF PARTICULAR PREFERRED EMBODIMENTS

Figure 1:
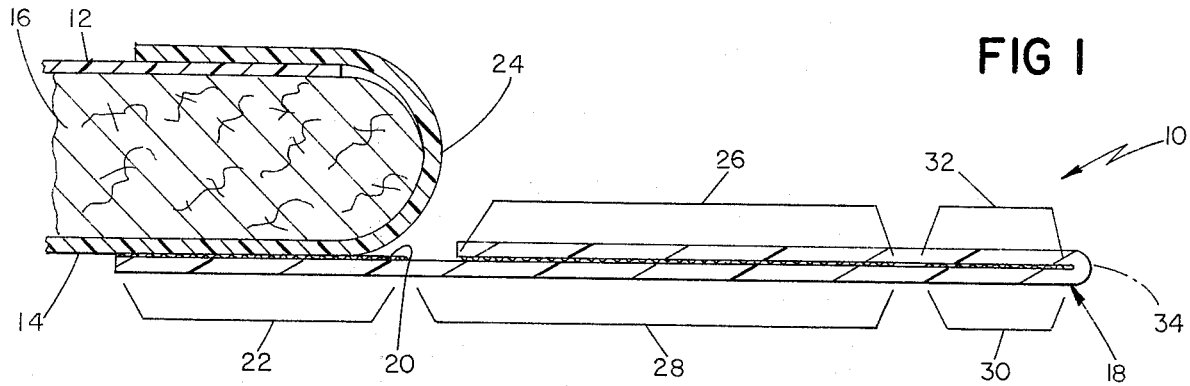
FIG. 1 is a longitudinal sectional view of one embodiment of a fastener constructed according to the present invention as provided on a diaper and prior to unfolding for use.

Referring to the drawings, the fasteners 10, 10a, 10b, and 10c are shown secured to a disposable diaper of conventional construction comprising a water pervious inner sheet 12, a water impervious outer sheet 14 and an absorbent body 16 sandwiched therebetween.

Figure 3:
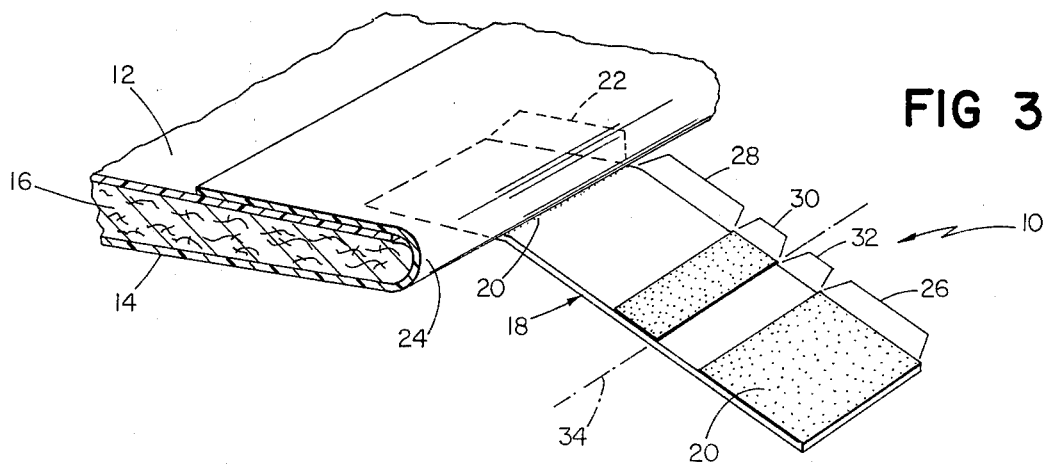
FIG. 3 is a perspective view of the fastener of FIG. 1 as unfolded for use.
Figure 4:
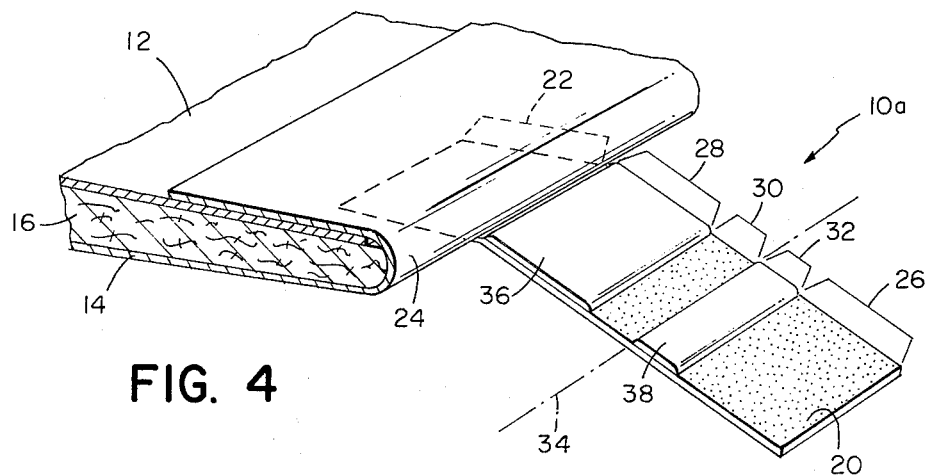
FIG. 4 is a perspective view of the fastener of FIG. 2 as unfolded for use.
Figure 5:
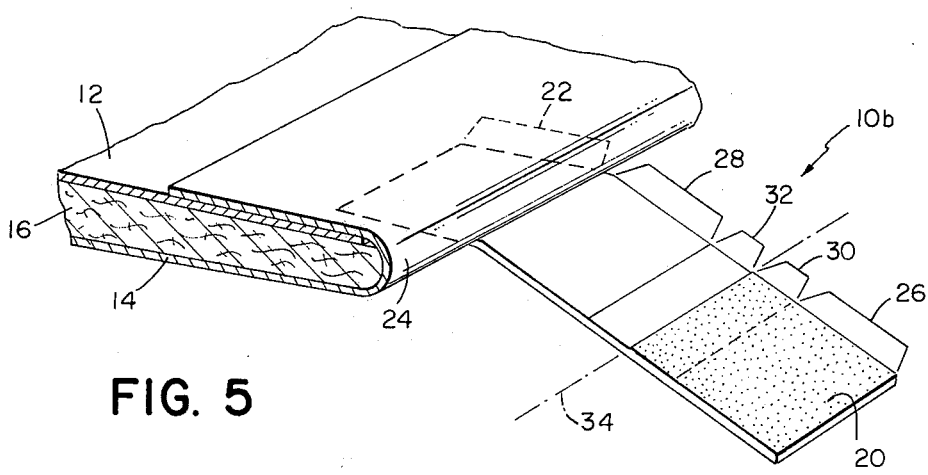
FIG. 5 is a view similar to FIG. 3 of an alternative embodiment.

Referring to FIGS. 1 and 3, the fastener 10 comprises a web 18 (e.g., a conventional plastic, cloth, or paper adhesive tape backing material) which may be viewed as divided into five separate longitudinally aligned zones. The inner surface of the web 18 is coated with an adhesive 20 in a first end zone 22 which is secured, by means of that adhesive 20, to the outer sheet 14 of the diaper adjacent the diaper lateral margin 24. The second end zone 26 is also adhesive coated for contact, after the fastener end has been unfolded as in FIG. 3, with the remote portion of the diaper for securing the diaper to an infant. Intermediate third, fourth, and fifth zones 28, 30, 32, (best seen in FIG. 3) are disposed between the two end zones. The fourth zone 32 is treated to have a reduced affinity for the adhesive 20 and the third zone 28 is treated to have a yet more reduced affinity for the adhesive, while the fifth zone 30 is an adhesive-coated zone. The zones 30 and 32 are the same size and the zones 26, 28 are the same size with the latter two zones being substantially larger than the former. Prior to use of the fastener (see FIG. 1), the web 18 is folded about a fold line 34 along the boundary between zones 30 and 32 thus bringing those two zones into contact with each other as well as bringing zones 26 and 28 into contact with each other. In the embodiment of FIG. 5, the positions of zones 30 and 32 are reversed.

Figure 2:
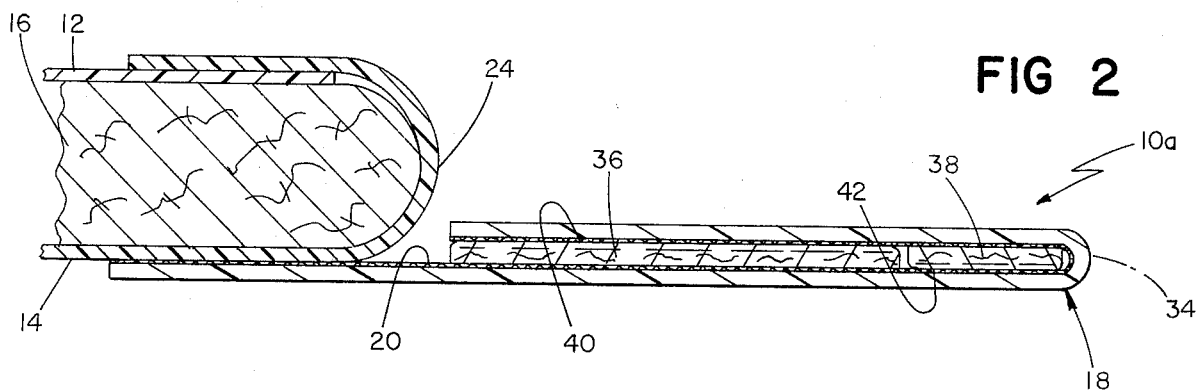
FIG. 2 is a view similar to FIG. 1 of a second embodiment of a fastener constructed according to the present invention.
Figure 6:
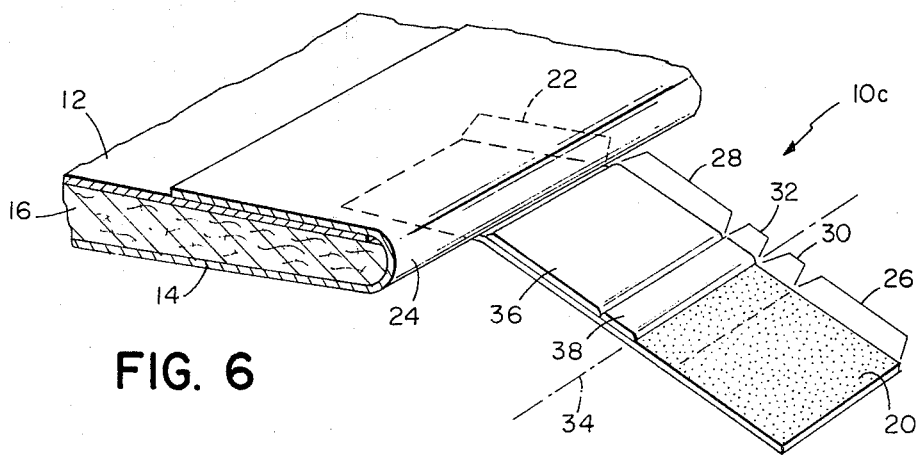
FIG. 6 is a view similar to FIG. 3 of another alternative embodiment.

In the embodiment shown in FIG. 2, the web 18 has its entire surface coated with the adhesive 20. The third and fourth zones are formed by the application of second and third webs (e.g., paper) 36, 38 to the web 18. The webs 36, 38 substantially fill the space between the opposed parallel segments of web 18. The surfaces of the webs 36, 38 which contact the adhesive 20 are untreated, thereby permitting their secure retention to the web 18. The exposed surfaces of the webs 36, 38 (i.e., surfaces 40, 42 respectively have been treated to have reduced affinity for the adhesive 20, the affinity of the surface 40 being even less than that of the surface 42. In the embodiment of FIG. 6 the positions of zones 30 and 32 are reversed.

In operation, the fastener 10, 10a, 10b, and 10c is presented to the consumer in a neat-appearing configuration (FIGS. 1, 2) in which the adhesive 20 is not exposed for premature contact with any object. The light adhesive bonds between the fourth and fifth zones 32, 30 is sufficient to maintain the fastener in the folded configuration while the extremely light bond between the second and third zones 26, 28 permits and facilitates the easy grasping of the web 18 in the zone 26 in order to unfold the fastener to the configuration shown in FIGS. 3–6. After the attachment of the diaper to the infant, the large third zone 28, adjacent the diaper of lateral margin 24, provides an adhesive-free region of the fastener 10 at the location in which accidental contact of the fastener 10 with the skin of the infant is most likely.

While particular preferred embodiments of the present invention have been illustrated in the accompanying drawing and described in detail herein, other embodiments are within the scope of the invention and the following claims.

I claim:

1. A fastener for a diaper comprising a length of web having a surface comprising a plurality of longitudinally aligned zones including a first end zone secured to a first portion of said diaper, a second end zone coated with an adhesive and securable to a second portion of said diaper, and third, fourth, and fifth intermediate zones, said fifth zone coated with an adhesive, each of said third and fourth zones being release treated to have a limited affinity for said adhesive, said web being folded such that said second and third zones are in contact and said fourth and fifth zones are in contact whereby the web portion comprising said second and fourth zones is releasably retained on the web portion comprising said third and fifth zones.

2. The fastener of claim 1 wherein said third zone has a lesser affinity for said adhesive than does said fourth zone.

3. The fastener of claim 1 wherein said third zone has a greater longitudinal dimension than does said fourth zone.

4. The fastener of claim 3 wherein said second and third zones have substantially equal longitudinal dimensions and said fourth and fifth zones have substantial equal longitudinal dimensions.

5. The fastener of claim 4 wherein said third zone has a lesser affinity for said adhesive than does said fourth zone.

6. The fastener of claim 1 wherein said fifth zone is intermediate said third and fourth zones.

7. The fastener of claim 1 wherein said fifth zone is adjacent said second zone.

8. A fastener for a diaper comprising a first length of web including an adhesive coated surface, a first end portion of said surface in contact with said diaper for securing said fastener thereto, a portion of said web adjacent the second end thereof folded back about a fold line to provide opposed parallel end and interior segments of said adhesive coated surface, second and third webs disposed between said segments, said second web having a first surface adhesively secured to said first web adjacent said fold line and its second surface release treated to have only a first partial affinity for said adhesive, said third web having a first surface secured to said interior segment at a location spaced apart from said fold line and its second surface release treated to have an affinity for said adhesive less than said first partial affinity whereby said web portion adjacent the second end is releasably retained on said release treated surfaces.

9. The fastener of claim 8 wherein said second and third webs substantially fill the space between said segments without overlap of said second and third webs.

10. The fastener of claim 9 wherein said second web is smaller than said third web.

11. The fastener of claim 8 wherein said second web first surface is adhesively secured to said end segment.

12. The fastener of claim 8 wherein said second web first surface is adhesively secured to said interior segment.

* * * * *